United States Patent
Dharmadhikari et al.

(10) Patent No.: US 8,426,470 B2
(45) Date of Patent: Apr. 23, 2013

(54) METHOD FOR ALLEVIATING SIGNS AND SYMPTOMS OF SPASTICITY

(75) Inventors: Nitin Bhalachandra Dharmadhikari, Mumbai (IN); Yashoraj Rupsinh Zala, Mumbai (IN)

(73) Assignee: Sun Pharmaceutical Industries Ltd., Mumbai (IN)

( * ) Notice: Subject to any disclaimer, the term of this patent is extended or adjusted under 35 U.S.C. 154(b) by 445 days.

(21) Appl. No.: 11/790,356

(22) Filed: Apr. 25, 2007

(65) Prior Publication Data

US 2007/0265343 A1 Nov. 15, 2007

(30) Foreign Application Priority Data

Apr. 26, 2006 (IN) .......................... 656/MUM/2006

(51) Int. Cl.
*A61K 31/195* (2006.01)
(52) U.S. Cl.
USPC ......................................................... 514/567
(58) Field of Classification Search .................. 514/567
See application file for complete search history.

(56) References Cited

U.S. PATENT DOCUMENTS 5,091,184 A * 2/1992 Khanna .......................... 424/435
2005/0090554 A1* 4/2005 Devane et al. ................ 514/567

FOREIGN PATENT DOCUMENTS

| WO | 03011255 A1 | 2/2003 |
| WO | WO 03/011255 A1 * | 2/2003 |
| WO | 2005101983 A2 | 11/2005 |

OTHER PUBLICATIONS

Dorland's Illustrated Medical Dictionary, 28th Edition, 1994 p. 1187.*
M. Merino et al., "Evidence of Specialized Absorption Mechanism for Baclofen", Proc. Eur. Congr. Biopharm. Parmacokinet, 3rd, Dept. of Pharm. and Pharmaceutics, Univ. of Valencia, Valencia, Spain, (1987), 2, pp. 564-573.
M. Merino et al., "Evidence of a Specialized Transport Mechanism for the Intestinal Absorption of Baclofen", Biopharmaceutics and Drug Disposition, vol. 10, No. 3, Dept. of Pharm. and Pharmaceutics, Faculty of Pharmacy, University of Valencia, Spain, (1989), pp. 279-297.
E. Knutsson et al., "Plasma and Cerebrospinal Fluid Levels of Baclofen (Lioresal®) at Optimal Therapeutic Responses in Spastic Paresis", Journal of the Neurological Sciences, vol. 23, (1974), pp. 473-484.

* cited by examiner

*Primary Examiner* — Jennifer M Kim
(74) *Attorney, Agent, or Firm* — Sughrue Mion, PLLC

(57) ABSTRACT

A method of alleviating signs and symptoms of spasticity in human patient comprising orally administering to said human patients once in a day a controlled drug delivery system comprising an effective daily dose of baclofen or its pharmaceutically acceptable salt. The controlled drug delivery system is operable to produce a level of sedation lower than a sedation produced by three times a day immediate release tablets. A total daily dosage of the controlled release tablets and a total daily dosage of the three times a day immediate release tablets remain same.

4 Claims, No Drawings

METHOD FOR ALLEVIATING SIGNS AND SYMPTOMS OF SPASTICITY

TECHNICAL FIELD

The present invention provides a method for alleviating the signs and symptoms of spasticity. Particularly, the present invention provides a method for alleviating the signs and symptoms of spasticity comprising orally administering once a day controlled drug delivery system of baclofen.

BACKGROUND OF THE INVENTION

Baclofen is an analog of the putative inhibitory neurotransmitter gamma-aminobutyric acid (GABA), and is chemically known as 4-amino-3-(4-chlorophenyl)-butanoic acid. It is a GABA-agonist that acts through presynaptic and postsynaptic pathways. The primary site of action is the spinal cord where baclofen reduces the release of excitatory neurotransmitters. It is used to help relax certain muscles in the body. Baclofen relieves the spasms, cramping, and tightness of muscles caused by medical problems such as multiple sclerosis, cerebral palsy, or certain injuries or diseases of the spine. It is approved worldwide for the alleviation of signs and symptoms of spasticity resulting from multiple sclerosis, particularly for the relief of flexor spasms and concomitant pain, clonus and muscular rigidity.

There is a wide inter-subject variation in the absorption and elimination of baclofen, but on an average it is rapidly and extensively absorbed after oral administration. Plasma elimination half-life of baclofen is approximately 3.5 hours (range 2 to 6 hours). Baclofen is excreted mainly by the kidneys in unchanged form although 15% is metabolized in the liver. Conventional baclofen therapy involves administration of immediate release tablets for example 10 mg or 20 mg immediate release tablets three times a day. The dose ranges from 30 mg to 100 mg/day in divided doses. Baclofen is also available in the USA for chronic use as an injection to be administered by the intrathecal route in single bolus test doses (via spinal catheter or lumbar puncture), and as implantable pumps approved by the Food and Drug Administration specifically for the administration of baclofen injection into the intrathecal space.

The term "immediate release baclofen tablets" as used herein means baclofen tablets that disintegrate in gastric fluids and release the baclofen into gastric fluids shortly thereafter. Frequent administration of immediate release baclofen tablets leads to fluctuations in plasma concentration producing peaks and troughs with peaks being associated with side effects, such as drowsiness (sedation), dizziness and muscle weakness and troughs causing inadequate control of muscle spasm. Side effects, like drowsiness and muscle weakness, are considered as major deterrents to the prescribers for up titration of the dosage for optimization of therapy. It is a matter of general concern, with conventional baclofen therapy, that the medication has to be administered frequently. Medication noncompliance among patients with medical illnesses has been reported to range from 15% to 85%. Although many factors are associated with medication noncompliance, it is thought that physicians can help promote compliance by prescribing medications that require a minimal number of doses. A once-a-day or twice-a-day (b.i.d.) dosage formulation with the same therapeutic effectiveness as the conventional baclofen therapy would vastly improve patients' compliance with treatment. These will also increase the outcome of therapy, as more number of patients will adhere to treatment plan.

However, prior art has taught that controlled, sustained or modified release systems that delay baclofen release beyond 8 hours may not be suitable. Merino et al, Proc. Eur. Congr. Biopharm. Pharmacokinet., $3^{rd}$ (1987), 2, 564-73, describes studies of intestinal absorption of baclofen in the rat small intestine. This reference concludes that administration of sustained-release forms of the drug or the use of increased doses of baclofen to obtain better therapeutic responses may not be suitable for clinical practice in humans.

Merino et al, Biopharmaceutics and Drug Disposition (1989), 10(3), 279-97, also describes studies of intestinal absorption of baclofen in the rat small intestine. The authors have recommended the administration of usual doses of baclofen at shorter intervals when higher plasma levels at steady-state are needed, and that more than 8-hour sustained-release preparations of baclofen should be avoided.

Baclofen crosses the blood brain barrier with concentrations in the cerebrospinal fluid (CSF) corresponding to about 12% of those in the plasma. The elimination half-life of baclofen from the CSF is about 4-5 hours. The amount of drug retained in the CSF is therefore responsible for providing the therapeutic effect of baclofen. The lowest concentration in plasma at which a significant reduction in spasticity was observed was 90 ng/ml (see "Plasma and cerebrospinal fluid levels of baclofen (Lioresal®) at optimal therapeutic response in spastic paresis"; Evert Knutsson, Ulf Lindblom and Anders Martensson, J. Neurological Sciences, 1974, 23: 473-484) Conventional release tablets, that are administered two or three times a day, provide peaks and valleys in the plasma concentration, and therefore, in the CSF concentration, which is not desirable. We tried to address this problem in our co-pending PCT application WO 03/011255A1 (the '255 application), which discloses an oral controlled drug delivery system for baclofen, and which is incorporated herein by reference. It exemplifies formulations that provide blood levels such that the system may be suitable for once a day administration. In our continued efforts to develop systems that provide better efficacy in alleviating the signs and symptoms of spasticity, we designed controlled drug delivery systems that provide higher plasma levels of baclofen than the systems of the '255 application (see our co-pending PCT application WO 2005/101983 A1 (the '983 application), which is incorporated herein by reference). Plasma levels higher than those provided by conventional baclofen therapy were achieved using the system of the '255 application, as well as the system of the '983 application, in healthy human volunteers. Thus, both of our systems were expected to provide better therapeutic efficacy as compared to conventional baclofen therapy, however, the increased plasma levels of baclofen were expected to give rise to more side effects associated with baclofen therapy, particularly on multiple dosing. Further, it was not known which of the systems would be preferred for clinical use of baclofen, for alleviating the signs and symptoms of spasticity in patients.

We have found a method for alleviating the signs and symptoms of spasticity by orally administrating once-a-day a controlled drug delivery system, which method surprisingly and unexpectedly provided statistically significant lower level of sedation, even on repeated or multiple dosing, than that associated with conventional baclofen therapy.

SUMMARY OF THE INVENTION

The present invention provides a method of alleviating signs and symptoms of spasticity in human patients comprising orally administering to said human patients once in a day a controlled drug delivery system comprising an effective daily dose of baclofen or its pharmaceutically acceptable salt wherein said method is associated with reduced level of sedation in said patients as compared to levels of sedation associated with conventional baclofen therapy with immediate release tablets administered three times a day on the same total daily dose.

DETAILED DESCRIPTION OF THE INVENTION

The present invention provides a method for alleviating signs and symptoms of spasticity by administering once in a day an oral controlled drug delivery system comprising a therapeutically effective amount of baclofen or its pharmaceutically acceptable salt. The once a day method for alleviating signs and symptoms of spasticity provides lower levels of sedation than levels of sedation associated with conventional baclofen therapy after repeated or multiple dosing. Surprisingly this is found in spite of the fact that pharmacokinetic studies revealed that plasma baclofen levels after single dose of the controlled drug delivery system were higher than the plasma levels after administration of the conventional baclofen therapy.

The once in a day controlled drug delivery system that is used in the present invention for alleviating signs and symptoms of spasticity comprises baclofen or its pharmaceutically acceptable salt in an amount sufficient to provide the desired therapeutic effect when administered once in a day. The system is designed to provide a controlled release of baclofen or its pharmaceutically acceptable salt. The term "controlled drug delivery system" as used herein means a drug delivery system that upon oral administration as a single dose provides to the systemic circulation baclofen, whose plasma concentration rises slowly and then declines slowly over a period of 24 hours to ranges of baclofen concentration during the first hour after oral administration of the system. For example, table 2 provides that at 24 hours the plasma concentration is about 33 ng/ml which is in the range from about 1 to about 80 ng/ml observed in the first hour.

The term spasticity as used herein includes spasticity of spinal and cerebral origin. The once a day method of the present invention is useful for alleviating signs and symptoms of spasticity arising from cerebrovascular accident, spinal injury, transverse myelitis, multiple sclerosis, spinal tuberculosis, non-compressive myelopathy, craniovertebral anomaly, spinal cord compression, spinal tumor, sub-acute combined degeneration and other causes that affect the spine.

"Pharmaceutically acceptable" as used herein, means those salts/excipients which are, within the scope of sound medical judgment, suitable for use in contact with the tissues of humans and lower animals without undue toxicity, irritation, allergic response, and the like, in keeping with a reasonable benefit/risk ratio, and effective for their intended use in the alleviating signs and symptoms of spasticity.

The daily dose of baclofen or its pharmaceutically acceptable salt that is used in the controlled drug delivery system of the present invention ranges from about 15 mg to about 80 mg. The amount of baclofen used is sufficient to provide relief in patients suffering from spasticity when administered orally once daily.

In a preferred embodiment, the controlled drug delivery system is the system disclosed in the '255 application. In another preferred embodiment, the controlled drug delivery system is the system disclosed in the '983 application.

A controlled drug delivery system, hereinafter referred to as System A, comprising baclofen was prepared according to the teachings of WO 2005/101983 A1, as mentioned in Table 1 below.

TABLE 1

| Ingredients | Quantity (mg/capsule) | Quantity (% w/w) |
|---|---|---|
| Capsule core | | |
| Baclofen | 17.5 | 1.83 |
| Mannitol SD 200 | 221.5 | 23.16 |
| Hydroxypropyl cellulose | 100.0 | 10.46 |
| Colloidal silicon dioxide | 5.0 | 0.52 |
| Talc | 10.0 | 1.05 |
| Magnesium stearate | 10.0 | 1.05 |
| Hydrogenated vegetable oil (Lubritab) | 20.0 | 2.10 |
| Mannitol SD 200 | 171.0 | 17.88 |
| Sub-coat (coated to a weight gain of about 25% w/w of the core) | | |
| Alginic acid | 66.35 | 6.94 |
| Sodium bicarbonate | 17.20 | 1.79 |
| Sodium starch glycolate | 33.17 | 3.47 |
| Mannitol 25 | 16.58 | 1.73 |
| Povidone (K-90F) | 23.55 | 2.46 |
| Talc | 4.30 | 0.45 |
| Polysorbate 20 | 1.35 | 0.14 |
| First coat (coated to weight gain of about 25% w/w of the sub-coated core) | | |
| Polycarbophil (Noveon AA1) | 8.95 | 0.94 |
| Eudragit L-100-55 | 66.15 | 6.92 |
| Sodium bicarbonate | 17.88 | 1.87 |
| Sodium starch glycolate | 21.50 | 2.25 |
| Mannitol 25 | 71.52 | 7.48 |
| Polyethylene glycol 400 | 2.69 | 0.28 |
| Diethyl phthalate | 8.95 | 0.94 |
| Polysorbate 20 | 1.07 | 0.11 |
| Top coat | | |
| Baclofen | 12.5 | 1.31 |
| Povidone K-30 | 7.00 | 0.73 |
| Talc | 19.50 | 2.04 |
| Polysorbate 20 | 1.0 | 0.104 |

Baclofen, mannitol, hydroxypropyl cellulose, colloidal silicon dioxide, talc and magnesium stearate were mixed and slugged. The slugs were then milled, mixed with Lubritab and mannitol SD 200, and filled into size 0 hard gelatin capsule. A 15% w/w coating solution (for the sub-coat) containing alginic acid, sodium bicarbonate, sodium starch glycolate, mannitol, povidone, talc and polysorbate 20 in isopropyl alcohol was prepared and coated onto the capsule to a weight gain of about 25% by weight of the capsule.

A 15% w/w coating solution (for the first coat) containing polycarbophil, Eudragit L-100-55, sodium bicarbonate, sodium starch glycolate, mannitol, polyethylene glycol 400, diethyl phthalate, polysorbate 20 and talc in isopropyl alcohol was coated onto to the sub-coated capsule to a weight gain of about 25% w/w. A 12% w/w coating solution (for the top coat) containing baclofen, povidone K-30, talc and polysorbate 20 in purified water was finally coated onto the coated capsule.

System B in the form of coated capsules containing 45 mg of baclofen was prepared in a manner similar to that described for system A above, with the same proportion of drug to individual excipients.

The bioavailability of baclofen from system A was compared with the immediate release tablets of baclofen (10 mg) administered three times a day. An open label, randomized, comparative and two-way crossover study was undertaken for the same.

The pharmacokinetic assessment was based on the plasma levels of baclofen measured by blood sampling. Blood samples were obtained before dosing and at the following times after dosing—0.5, 1.0, 1.5, 2, 3, 4, 6, 8, 8.5, 9, 9.5, 10, 11, 12, 14, 16, 16.5, 17, 18, 19, 20, 22, 24, 30 aid 36 hours.

Fourteen healthy male volunteers were enrolled for the study and all of them completed the study. The subjects were fasted overnight and were given a high-fat meal 30 minutes before dosing. No food was allowed for at least 4 hours post-dose. Drinking water was prohibited 2 hours before dosing and 2 hours thereafter, but was allowed ad lib all other times. Standard meals were provided at 4, 8 and 12 hours after dosing and at appropriate times thereafter. During housing, meal plans were identical for both the periods.

Subjects received the composition of System A comprising 30 mg of baclofen with 240 ml of water at ambient temperature after the fast, as the test medication. The conventional baclofen therapy was with baclofen immediate release tablets of Ciba Labs, England, comprising 10 mg baclofen, administered three times in a day. The first dose was given 30 minutes after the high-fat meal, while the other two doses were given at 8 and 16 hours without any special diet.

The plasma concentration of baclofen was determined for samples collected at different time points and averaged over the fourteen volunteers. The data is given in Table 2 below.

TABLE 2

| | Mean Plasma concentration (ng/ml) of baclofen | |
|---|---|---|
| Time (hours) | Test (System A, single dose) | Conventional therapy (3 × 10 mg tablets of Ciba) |
| 0 | 0.75 | 0.25 |
| 0.5 | 38.08 | 32.07 |
| 1.0 | 78.16 | 70.46 |
| 1.5 | 112.57 | 104.63 |
| 2.0 | 135.11 | 108.16 |
| 3.0 | 161.50 | 101.04 |
| 4.0 | 162.71 | 86.44 |
| 6.0 | 182.33 | 58.25 |
| 8.0 | 171.54 | 37.51 |
| 8.50 | 168.39 | 39.76 |
| 9.00 | 151.71 | 49.78 |
| 9.50 | 138.71 | 66.01 |
| 10.00 | 131.59 | 76.82 |
| 11.00 | 116.59 | 96.71 |
| 12.00 | 111.59 | 101.51 |
| 14.00 | 95.24 | 81.76 |
| 16.00 | 76.24 | 62.76 |
| 16.50 | 75.06 | 70.21 |
| 17.00 | 69.26 | 88.95 |
| 18.00 | 61.19 | 122.84 |
| 19.00 | 55.86 | 124.61 |
| 20.00 | 51.83 | 110.67 |
| 22.00 | 42.21 | 83.56 |
| 24.00 | 32.68 | 59.27 |
| 30.00 | 14.31 | 23.24 |
| 36.00 | 7.80 | 11.23 |

The pharmacokinetic parameters calculated using the Win Nonlin software are given in Table 3 below.

TABLE 3

| | | Ln-transformed | |
|---|---|---|---|
| | | Least Square Means | |
| Parameter | Units | Test (System A 30 mg, single dose) | Reference (3 × 10 mg tablets of Ciba) |
| $C_{max}$ | ng/ml | 202.07 | 146.22 |
| $AUC_{0-t}$ | ng · hr/ml | 2692.07 | 2285.51 |
| $AUC_{0-inf}$ | ng · hr/ml | 2755.34 | 2368.10 |

It was found that for most of the period from the time of administration up to about 16 hours, the plasma levels of baclofen were higher for System A of the present invention. However, from 16 hours onwards to 24 hours, the plasma levels were higher for the immediate release tablets given three times a day. The peak plasma level obtained with System A of the present invention was higher than peak plasma level obtained after administration of immediate release tablets given three times a day.

A controlled drug delivery system, hereinafter referred as System C, was prepared as per the teachings of WO 03/011255A1 and as mentioned in Table 4 below.

TABLE 4

| Ingredients | Quantity (mg/tablet) | Quantity (% w/w) |
|---|---|---|
| Core | | |
| Intragranular | | |
| Baclofen | 22.5 | 2.25 |
| Mannitol 60 | 260.0 | 2.04 |
| Hydroxyethyl cellulose (HEC 250 HX Pharma) | 200.0 | 20.03 |
| Sodium starch glycolate | 250.0 | 25.04 |
| Sodium bicarbonate | 80.0 | 8.01 |
| Hydroxypropyl methylcellulose (HPMC K4M) | 4.50 | 0.45 |
| Extragranular | | |
| Silicified microcrystalline cellulose (Prosolv SMCC 90) | 90.0 | 9.01 |
| Talc | 24.0 | 2.40 |
| Polyethylene glycol (PEG 8000) | 10.0 | 1.00 |
| Coat | | |
| Baclofen | 7.5 | 0.75 |
| Hydroxypropyl methylcellulose (HPMC E5) | 24.0 | 2.40 |
| Talc | 10.0 | 1.00 |
| Propylene glycol | 5.0 | 0.5 |
| Titanium dioxide | 11.0 | 1.10 |

The core of the controlled drug delivery system (system C) was obtained by passing baclofen, mannitol, hydroxyethyl cellulose, sodium starch glycolate and sodium bicarbonate through ASTM (American Society for Testing and Materials) sieve #40 and mixing the ingredients to obtain a dry powder blend. An aqueous solution HPMC K4M was then used to granulate the dry powder blend. The granules thus obtained were passed through a suitable sieve and dried. The dry granules were lubricated with a mixture of Prosolv SMCC 90, talc and PEG 8000, and compressed to obtain the cores. The cores were then coated with a hydroalcoholic solution of a mixture of baclofen, HPMC E5, talc, propylene glycol and titanium dioxide to obtain the controlled drug delivery system of the present invention.

The tablets thus obtained were subjected to dissolution testing at 37° C. using United States Pharmacopoeia Type II (paddle) dissolution apparatus at 50 rpm. The dissolution medium used was 1000 ml of 0.1N HCl. The tablets achieved floatation in about 6 minutes. The results of the dissolution test are recorded in Table 5 below.

TABLE 5

| Time | % baclofen released in 0.1N HCl |
|---|---|
| 0 | 0 |
| 1 | 55 |
| 2 | 63 |
| 4 | 75 |
| 6 | 83 |
| 8 | 91 |
| 12 | 99 |

The pharmacokinetics of baclofen after administration of the controlled drug delivery system C comprising 30 mg baclofen was studied in comparison to immediate release tablets given three times a day. An open label, randomized, comparative, two-way crossover study was undertaken for the same.

The pharmacokinetic assessment was based on the plasma levels of baclofen measured by blood sampling. Blood samples were obtained before dosing and at the following times after administration of the test medication—0.25, 0.5, 1, 1.5, 2, 2.5, 3, 4, 6, 8, 12, 12.5, 13, 13.5, 14, 15, 16, 20 and 24 hours.

Twelve healthy male volunteers were enrolled for the study and all of them completed the study. The subjects were fasted overnight and were given a high fat breakfast before dosing. Drinking water was prohibited 2 hours before dosing and 2 hours thereafter, but was allowed ad lib at all other times. Standard meals were provided at 4 hours and 8 hours after dosing and at appropriate times thereafter. Meal plans were identical for both the periods.

Subjects received a single tablet of baclofen (System C, 30 mg) with 240 ml of water at ambient temperature after the fast, for five days.

The plasma concentration of baclofen was determined for samples collected at different time points and averaged over the twelve volunteers. The data is given in Table 6 below.

TABLE 6

| Time (hours) | Mean Plasma concentration (ng/ml) of baclofen controlled drug delivery system (System C, 30 mg) |
|---|---|
| 0 | 0 |
| 0.25 | 0.97 |
| 0.5 | 12.95 |
| 1.0 | 81.57 |
| 1.5 | 117.42 |
| 2.0 | 141.46 |
| 2.5 | 154.1 |
| 3.0 | 157.67 |
| 4.0 | 172.88 |
| 6.0 | 155.77 |
| 8.0 | 119.55 |
| 12.0 | 67.38 |
| 12.5 | 65.28 |
| 13.0 | 60.20 |
| 13.5 | 57.01 |
| 14.0 | 52.26 |
| 15.0 | 48.18 |
| 16.0 | 40.07 |
| 20.0 | 28.03 |
| 24.0 | 18.87 |

System D, i.e. controlled drug delivery system, containing 45 mg of baclofen was prepared in a manner similar to that described for system C above, with the same proportion of drug to individual excipients.

The compositions of system A and B (Group A) and systems C and D (Group B) were subjected to clinical study in patients with neurological spasticity, who were stabilized on conventional baclofen therapy (immediate release (IR) tablets given three times a day) on the same total daily dose in mg. The clinical trial was designed to be a randomized (1:1), controlled, parallel-group, multicenter, double blind trial, carried out over a period of 4 weeks. The safety evaluation for treatment emergent adverse events was done on patients in both the groups. A total of 90 patients (male and female patients aged between 18 and 65 years) were enrolled at 8 trial sites. Patients already stabilized on baclofen IR (30-60 mg/day) were randomized to either of the two treatment groups by randomized sequence, stratified for each dosage level. The switchover from IR formulation to Group A or Group B was at the same dose level.

Patients randomized to Group A received one capsule of system A and B (30 mg or 45 mg) per day for 4 weeks. Patients randomized to Group B received one tablet of system C and D (30 mg or 45 mg) per day for 4 weeks. The trial medication was given in the morning before breakfast on an empty stomach.

The primary analysis variable was the adjusted mean change in Ashworth rigidity scale score at the end of the treatment period compared to the conventional baclofen therapy, which was considered the baseline. Two values were considered per patient per treatment: i.e. baseline value (with conventional baclofen therapy) and the end of 4-week treatment value. In patients treated with System C, the Ashworth scale score decreased favorably on visit 5 by 0.37 (standard deviation 0.49) and in the patients treated with system A the decrease in Ashworth scale score 0.37 (standard deviation 0.50). Table 7 shows the endpoint analysis of primary efficacy variable.

TABLE 7

| Variable | Group A (System A) | Group B (System C) |
|---|---|---|
| Ashworth Rigidity Score | | |
| Initial | 3.07 ± 0.76 | 3.01 ± 0.74 |
| Final | 2.71 ± 0.63 | 2.64 ± 0.68 |
| Change | −0.37 ± 0.50 | −0.37 ± 0.49 |

The sedation score analysis of Group A and Group B is recorded in Table 8 below.

TABLE 8

| Sedation score | Group A (System A) | Group B (System C) |
|---|---|---|
| Initial | 8.14 ± 10.29 | 10.36 ± 9.24 |
| Final | 5.33 ± 7.28 | 6.07 ± 6.24 |
| Change | −2.81 ± 7.57 | −4.29 ± 8.65 |
| Significance (Initial v Final) (Wilcoxon signed ranks test) | 0.019 | 0.002 |

It is evident from the table above that surprisingly both groups had statistically and clinically significant improvement over baclofen IR (i.e. baseline) with respect to sedation score, even after multiple dosing. Thus, both have superior sedation profile and are thus safer compared to baclofen IR, despite the higher plasma levels provided by the controlled drug delivery systems.

While the invention has been described by reference to specific embodiments and references incorporated herein, this was done for purposes of illustration only and should not be construed to limit the spirit or the scope of the invention. Inasmuch as the foregoing specification comprises preferred embodiments of the invention, it is understood that variations and modifications may be made herein, in accordance with the inventive principles disclosed, without departing from the scope of the invention.

What is claimed is:

1. A method of alleviating signs and symptoms of spasticity in human patients, said method comprising orally administering to said human patients an once-a-day controlled drug delivery system comprising an effective daily dose of baclofen or its pharmaceutically acceptable salt, wherein the controlled drug delivery system produces a level of sedation lower than a sedation produced by three times a day immediate release tablets, wherein a total daily dosage of the controlled release tablets and a total daily dosage of the three times a day immediate release tablets remain the same.

2. A method as claimed in claim 1, wherein the daily dose of baclofen or its pharmaceutically acceptable salt ranges from about 15 mg to about 80 mg.

3. A method as claimed in claim 2, wherein the daily dose of baclofen is 30 mg.

4. A method as claimed in claim 2, wherein the daily dose of baclofen is 45 mg.

\* \* \* \* \*